(12) United States Patent
Bockenstedt et al.

(10) Patent No.: US 11,717,335 B2
(45) Date of Patent: Aug. 8, 2023

(54) PAIN MITIGATION BY MECHANICAL STIMULATION WHEN TREATING TISSUE WITH ELECTROMAGNETIC ENERGY

(71) Applicant: Solta Medical Ireland Limited, Dublin (IE)

(72) Inventors: Craig Robert Bockenstedt, Bothell, WA (US); Gregory T. Wing, Carnation, WA (US)

(73) Assignee: Sola Medical Ireland Limited, Dublin (IE)

( * ) Notice: Subject to any disclaimer, the term of this patent is extended or adjusted under 35 U.S.C. 154(b) by 287 days.

(21) Appl. No.: 16/556,664

(22) Filed: Aug. 30, 2019

(65) Prior Publication Data

US 2020/0069356 A1 Mar. 5, 2020

Related U.S. Application Data

(60) Provisional application No. 62/725,555, filed on Aug. 31, 2018.

(51) Int. Cl.
*A61B 18/00* (2006.01)
*A61B 18/12* (2006.01)
*A61B 18/18* (2006.01)
*A61B 18/14* (2006.01)

(52) U.S. Cl.
CPC .......... *A61B 18/1206* (2013.01); *A61B 18/18* (2013.01); *A61B 2018/00452* (2013.01); *A61B 2018/00577* (2013.01); *A61B 2018/00642* (2013.01); *A61B 2018/00791* (2013.01); *A61B 2018/126* (2013.01); *A61B 2018/128* (2013.01); *A61B 2018/1253* (2013.01); *A61B 2018/1266* (2013.01)

(58) Field of Classification Search
CPC ................ A61B 18/1206; A61B 18/18; A61B 2018/00577; A61B 2018/126; A61B 2018/00642; A61B 2018/1253; A61B 2018/00791; A61B 2018/00452; A61B 2018/128; A61N 2018/1266
See application file for complete search history.

(56) References Cited

U.S. PATENT DOCUMENTS 4,979,952 A * 12/1990 Kubota ............ A61B 17/22012
310/316.01
8,506,506 B2 * 8/2013 Nebrigic ................ A61B 18/18
607/100
8,906,009 B2 * 12/2014 Nebrigic ................ A61B 18/18
606/33

(Continued)

*Primary Examiner* — Kaitlyn E Smith
*Assistant Examiner* — Annie L Shoulders
(74) *Attorney, Agent, or Firm* — Thompson Hine LLP

(57) ABSTRACT

Apparatus and methods for delivering electromagnetic energy to a patient's tissue and reducing pain experienced by the patient during treatment of the patient's tissue with the delivered electromagnetic energy. The tissue treatment apparatus includes a delivery device configured to transfer the electromagnetic energy through the skin surface to a region of tissue, and also includes a vibration device that is mechanically coupled with the delivery device. The vibration device is configured to transfer mechanical vibrations along an axis substantially normal to the skin surface to the region of tissue being treated.

8 Claims, 4 Drawing Sheets

(56) References Cited

U.S. PATENT DOCUMENTS

| | | | |
|---|---|---|---|
| 2009/0157094 A1* | 6/2009 | Yeshurun | A61B 17/54 606/131 |
| 2010/0179455 A1* | 7/2010 | Nebrigic | A61B 18/18 606/33 |
| 2013/0304053 A1* | 11/2013 | Nebrigic | A61H 23/0263 606/33 |
| 2017/0202580 A1* | 7/2017 | Yoshimine | A61B 17/1675 |

* cited by examiner

PAIN MITIGATION BY MECHANICAL STIMULATION WHEN TREATING TISSUE WITH ELECTROMAGNETIC ENERGY

CROSS-REFERENCE TO RELATED APPLICATIONS

This application claims the benefit of U.S. Provisional Application No. 62/725,555, filed Aug. 31, 2018, the content of which is fully incorporated by reference herein in its entirety.

FIELD OF THE INVENTION

The invention generally relates to apparatus and methods for treating tissue with high frequency energy and, more particularly, relates to treatment apparatus and methods for reducing patient pain with mechanical stimulation while treating tissue with high frequency energy.

BACKGROUND

Various cosmetic tissue treatments use energy delivery devices to treat tissue in order to improve a patient's appearance, such as smoothing and tightening skin, contouring along the jaw line and under the chin, and improving skin texture; softening wrinkles around the mouth, eyes and forehead; reducing cellulite; or removing skin spots or hair. These non-invasive, transcutaneous procedures involve no surgery or injections, but instead project electromagnetic energy into the tissue. Such non-invasive energy delivery devices may emit the electromagnetic energy in different regions of the electromagnetic spectrum to accomplish the tissue treatment with reduced patient recovery time in comparison with ablative procedures.

Skin is a type of body tissue that includes plural distinct layers. The epidermis constitutes the visible outer layer on the surface. The dermis, which underlies the epidermis, contains collagen fibers, blood vessels, hair follicles, and other skin components. The hypodermis or subcutaneous fat layer, which underlies the dermis, consists of fat tissue and a web of collagen fibers in the form of fibrous septae running through the fat. The fibrous septae secure the dermis to the underlying bone and muscle. Collagen fibers are recognized to be a very flexible and stretchable protein and are characterized by a high tensile strength.

The occurrence of wrinkles is an unavoidable natural process. Wrinkles are primarily associated with advancing age and skin damage arising from exposure to damaging environmental factors. Environmental factors include sun damage from exposure to sunlight, air pollution, smoking, repetitive facial movements such as frowning, and the natural effects of gravity, which cause sagging of the skin with advancing aging. Deteriorating collagen exhibits a loss of elasticity, which results in the formation of rhytids or wrinkling of the epidermis.

Electromagnetic radiation, specifically light and heat, applied to the different layers of the skin can have a physiological effect on the skin's appearance. In particular, electromagnetic energy can arrest the formation of wrinkles and impart a more youthful skin appearance. High frequency treatment devices, such as radio-frequency (RF)-based treatment devices, may be used to treat skin tissue non-ablatively and non-invasively with heat. Such high frequency devices operate by transmitting high frequency energy through the epidermis to the underlying tissue, while actively cooling the epidermis to prevent thermal damage to a depth of the skin tissue near the skin surface. The high frequency energy heats the tissue at depths beneath the cooled region to a therapeutic temperature sufficient to denature the collagen, which causes the collagen fibers in the dermis to shrink and contract. In addition to the tightening of the treated tissue as the collagen fibers contract, treatment with high frequency energy also causes a mild inflammation. The inflammatory response of the treated tissue may cause new collagen to be generated over time, which can result in additional tissue contraction. When the inflammatory response of the treated tissue is highly significant, the new collagen formed is known as scar collagen.

Conventional high frequency treatment devices employ a handpiece, a disposable treatment tip coupled with a nose of the handpiece, and a high frequency generator connected by conductors inside the handpiece with an electrode in the treatment tip. Conventional electrodes consist of a pattern of one or more metallic features carried on a flexible electrically insulating substrate, such as a thin film of polyimide. The substrate contacts the patient's skin surface during treatment and the metallic features reside on the non-contact side of the substrate. The temperature of the treatment tip, which is measured by temperature sensors carried on the treatment tip, is correlated with the temperature of the patient's skin. During the procedure, the doctor controls the energy density of the high frequency power delivered from the electrode with a treatment setting. Treatment tips are frequently intended for single patient use and, therefore, are not reusable. Following the patient treatment, the doctor or treatment technician removes the treatment tip from the handpiece and, if disposable, discards it.

Patient pain is inherent in tissue treatments using electromagnetic energy. Patient pain is typically regulated to optimize the treatment result while also minimizing patient discomfort to make the procedure tolerable. A patient may be given an oral pain medication and/or a local topical anesthesia cream may be applied as a numbing agent. At the inception of the treatment procedure, the doctor will initially administer the high frequency energy at a treatment setting to one or more test sites and monitor patient feedback on the heat sensation associated with the treatment setting being used. A tolerable, yet comfortable, treatment setting for the treatment procedure is established based upon the patient feedback from the test sites.

The treatment electrode used in the treatment includes a conductor region delimited by an outer peripheral edge. For monopolar energy delivery, an edge effect has been observed at the outer peripheral edge that causes the energy density of the high frequency energy delivered to the tissue to be non-uniform across the surface area of the treatment electrode. Specifically, the energy density is highest near the peripheral edge of the electrode. As a result, tissue proximate to the outer peripheral edge of the electrode is heated to a higher temperature than tissue proximate to the interior surface area of the electrode. The higher temperatures near the peripheral edge form hot spot thermal zones that are a highly likely source of heat-related pain perceived by the patient. Because patient discomfort is linked with the treatment setting, reducing the treatment level to counteract the edge effect effectively reduces the average energy density for the high frequency energy delivered during the treatment procedure.

Previous attempts at reducing the pain associated with such tissue treatments so that patient discomfort is alleviated and therapeutic results can be improved used a vibrating device mechanically coupled with the delivery device. However, these apparatuses often use complex systems to effect the vibration and/or fail to control the direction in which the vibration occurs.

What is needed, therefore, are improved apparatuses and methods for reducing the pain associated with such tissue treatments to allow for the alleviation of patient discomfort and improvement of therapeutic results.

SUMMARY

Apparatus and methods are described herein for transcutaneously delivering electromagnetic energy to treat tissue underlying a skin surface, particularly during therapeutic tissue treatments that may be non-invasive and non-ablative, with reduced patient pain.

In an embodiment, a tissue treatment apparatus for use in treating a region of tissue located beneath a skin surface with electromagnetic energy includes a delivery device configured to transfer the electromagnetic energy through the skin surface to the region of tissue and a vibration device mechanically coupled with the delivery device. The vibration device is configured to transfer mechanical vibrations through the skin surface to the region of tissue along an axis substantially normal to the skin surface.

In an embodiment, a method includes vibrating a delivery device configured to transfer an electromagnetic energy through a skin surface to a region of tissue. Vibration is in a direction along an axis substantially normal to the skin surface.

BRIEF DESCRIPTION OF THE DRAWINGS

The accompanying drawings, which are incorporated in and constitute a part of this specification and in which like reference numerals refer to like features, illustrate embodiments of the invention and, together with a general description of the invention given above and the detailed description of the embodiments given below, serve to explain the principles of the invention.

DETAILED DESCRIPTION

Figure 1:
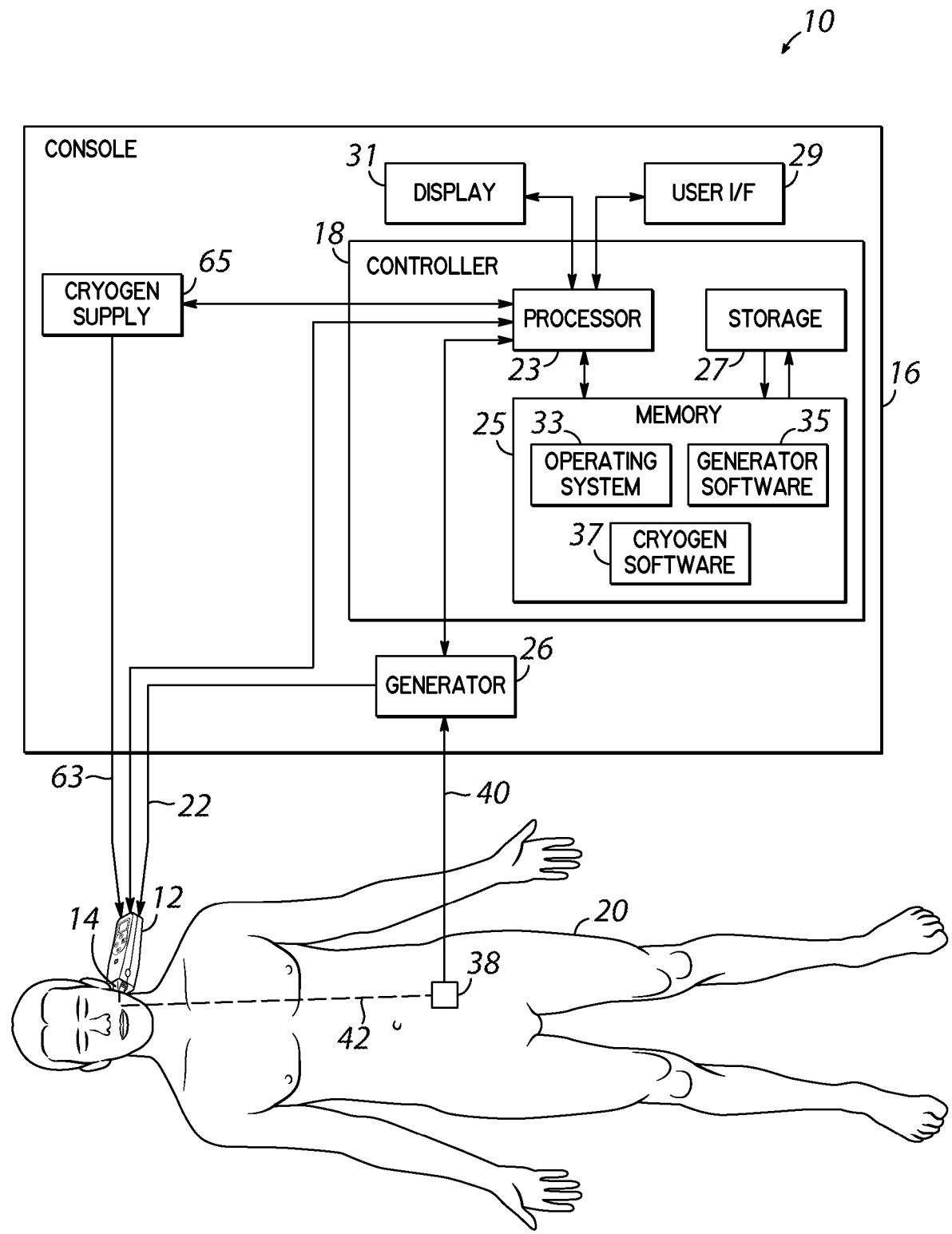
FIG. 1 is a diagrammatic view of a treatment system with a handpiece, a treatment tip, a console, and a generator in accordance with an embodiment of the invention.
Figure 6:
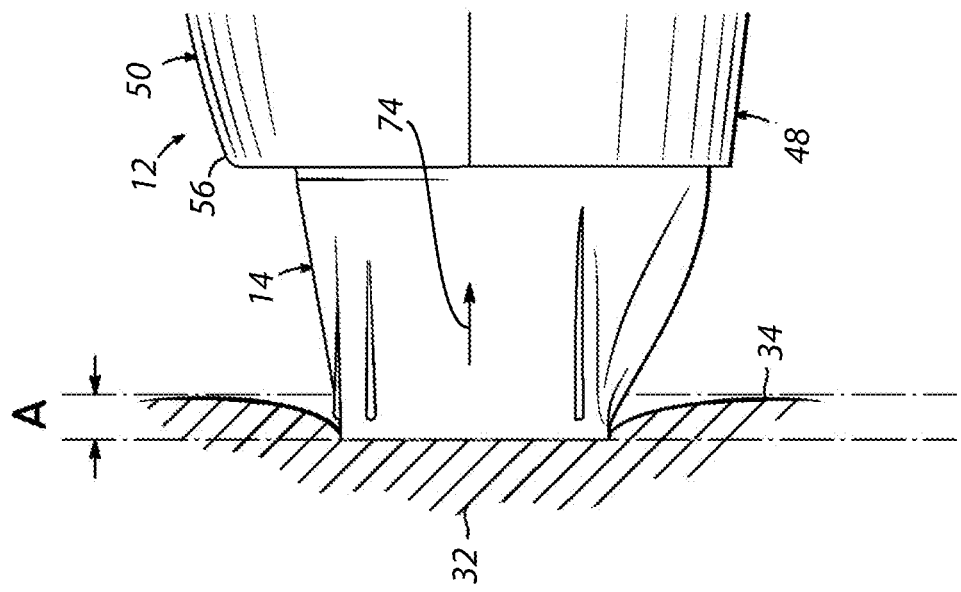
FIGS. 5 and 6 are detailed views of the treatment tip in use during a treatment procedure conducted using the treatment system of FIGS. 1-4.
Figure 5:
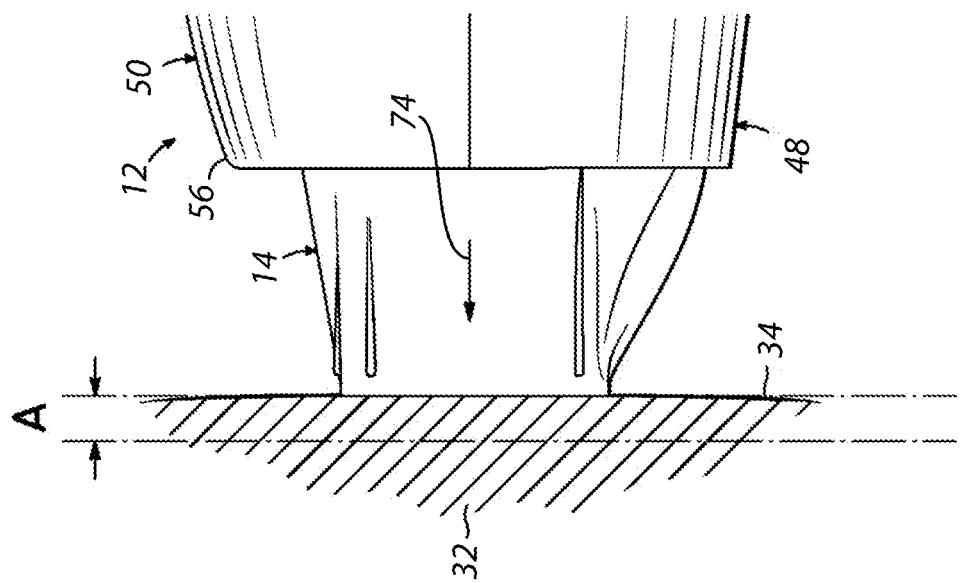

Referring now to the drawings, FIG. 1 shows a treatment apparatus 10 that generally includes a handpiece 12, a treatment tip 14 that may be coupled in a removable and releasable manner with the handpiece 12, a console generally indicated by reference numeral 16, and a system controller 18. The system controller 18, which is incorporated into the console 16, orchestrates the global operation of the different individual components of the treatment apparatus 10. Under the control of the system controller 18 and any operator interaction with the system controller 18 at the console 16 and with controls at the handpiece 12, the treatment apparatus 10 is adapted to deliver electromagnetic energy in a high frequency band of the electromagnetic spectrum to a region of a patient's tissue 32 (FIGS. 5 and 6). The delivered electromagnetic energy heats the tissue 32 to a targeted temperature range over a given tissue depth. The elevation in temperature will produce for example, changes in collagen fibers that achieve a desired treatment result, such as removing or reducing wrinkles and otherwise tightening the skin to thereby improve the appearance of a patient 20 receiving the treatment.

The treatment tip 14 may provide, either alone or in combination with the handpiece 12, an energy delivery member that includes a treatment electrode 24. The generator 26 is configured to generate the electromagnetic energy used in the treatment to impart a therapeutic effect by heating target tissue 32 beneath the patient's skin surface 34. The generator 26, which has the form of a high frequency power supply, is equipped with an electrical circuit operative to generate high frequency electrical current, typically in the radio-frequency (RF) band of the electromagnetic spectrum. The electrical circuit in the generator 26 converts a line alternating current voltage into drive signals for the treatment electrode 24. The drive signals have an energy content and a duty cycle appropriate for the amount of power and the mode of operation that have been selected by the clinician. In alternative embodiments, the treatment apparatus 10 may be configured to deliver energy in the infrared band, microwave band, or another high frequency band of the electromagnetic spectrum, rather than within the RF band, to the patient's tissue 32.

The system controller 18 may include at least one processor 23 coupled to a memory 25, which is non-transitory memory. The at least one processor 23 may represent one or more microprocessors, and the memory 25 may represent the random access memory (RAM) comprising the main storage of system controller 18, as well as any supplemental levels of memory, e.g., cache memories, non-volatile or backup memories (e.g., programmable or flash memories), read-only memories, etc. In addition, memory 25 may be considered to include memory storage physically located elsewhere in system controller 18, e.g., any cache memory, as well as any storage capacity used as a virtual memory, e.g., as stored on a mass storage device 27 or another computer (not shown) coupled to system controller 18 via a network.

The system controller 18 also typically receives a number of inputs and outputs for communicating information externally. For interface with a user or operator, system controller 18 typically includes one or more user input devices (e.g., a keyboard, a mouse, a trackball, a joystick, a touch screen, a keypad, a stylus, and/or a microphone, among others) in the form of a user interface 29. The user interface 29 may be used to deliver instructions to the system controller 18 to adjust the generator 26 and to establish an arbitrary treatment setting based upon operator input at the handpiece 12. System controller 18 may also include a display 31 (e.g., a CRT monitor or an LCD display panel, among others).

System controller 18 operates under the control of an operating system 33, and executes or otherwise relies upon various computer software applications, components, programs, objects, modules, data structures, etc. In general, the routines executed by the system controller 18 to operate the treatment apparatus 10, whether implemented as part of an operating system or a specific application, component, program, object, module or sequence of instructions will be referred to herein as "computer program code." The computer program code typically comprises one or more instructions that are resident at various times in various memory and storage devices in a computer, and that, when read and executed by one or more processors in a computer, causes that computer to perform the steps necessary to execute steps or elements embodying the various aspects of the invention.

The system controller 18 includes digital and/or analog circuitry that interfaces the processor 23 with the generator 26 for regulating the power delivered from the generator 26 to the treatment electrode 24. Generator software 35 resides as an application i.e., program code) in the memory 25 and is executed by the processor 23 in order to issue commands that control the operation of the generator 26. The system controller 18 includes digital and/or analog circuitry that interfaces the processor 23 with a cryogen supply 65, such as a system configured to deliver pressurized cryogen to a control valve (not shown) at the handpiece 12 and to control the control valve for regulating the cryogen delivered to the treatment electrode 24. Cryogen software 37 resides as an application i.e., program code) in the memory 25 and is executed by the processor 23 in order to issue commands that control the operation of the cryogen supply 65 and the control valve 79.

With reference now to FIGS. 2-6, during a tissue treatment involving the treatment electrode 24, the substrate 30 is arranged between the conductor region 28 and the skin surface of the patient. Electromagnetic energy may be transmitted in a transcutaneous manner from the conductor region 28 through the thickness of substrate 30 and across the surface area of the portion to the tissue by capacitively coupling with the tissue of the patient 20.

The treatment tip 14 includes temperature sensors (not shown), such as thermistors or thermocouples, that are constructed to detect the temperature of the treatment electrode 24 and/or treatment tip 14. The measured temperature reflects the temperature of the treated tissue 32 and may be used as feedback in a control loop controlling energy delivery and/or cooling of the skin surface. The handpiece 12 or treatment tip 14 may also include pressure sensors (not shown) for detecting physical contact between the treatment electrode 24 and the skin surface 34 of the patient 20.

An activation button 36, which is accessible to the operator from the exterior of the handpiece 12, is configured to be actuated to close a switch in a normally open circuit with the generator 26. The closed circuit energizes the treatment electrode 24. Actuation of the activation button 36 triggers delivery of the high frequency energy over a short timed delivery cycle to the target tissue 32. After a fixed amount of time has elapsed, the delivery of high frequency energy from the treatment electrode 24 to the tissue 32 at the treatment site is discontinued. The handpiece 12 is manipulated to position the treatment tip 14 near a different treatment site on the skin surface 34 and another cycle of high frequency energy is delivered to the patient's tissue 32. This process is repeated for an arbitrary number of treatment sites.

High frequency electrical current flowing between the treatment electrode 24 and the patient 20 is concentrated at the skin surface 34 and the underlying tissue 32 across the contacting surface area of the treatment electrode 24. Capacitive coupling of the high frequency electromagnetic energy relies on energy transfer from the conductor region (not shown) through the dielectric material of the substrate 30 to create an electric field across the surface area where the treatment electrode 24 contacts the patient's body. The time-varying electric field induces electrical currents within the surrounding tissue 32 beneath the skin surface 34.

Because of the natural resistance of tissue 32 to electrical current flow, volumetric heating results within the tissue 32. The volumetric heating delivers a therapeutic effect to the tissue 32 near the treatment site. For example, heating to a temperature of 50° C. or higher will contract collagen, which will result in tissue tightening or another aesthetic effect to improve the patient's appearance. The heating depth in the tissue 32 is based upon the size and geometry of the treatment electrode 24 and, contingent upon the selection and configuration of the treatment tip 14, can be controlled to extend from a few hundred micrometers beneath the skin surface 34 to several millimeters.

A non-therapeutic passive return electrode 38 (FIG. 1) may be used to electrically couple the patient 20 with the generator 26. During patient treatment, the high frequency current flows from the treatment electrode 24 through the treated tissue 32 and the intervening bulk of the patient 20 to the return electrode 38 and then to the generator 26 through conductors inside a return cable 40 to define a closed circuit or current path 42. The return electrode 38 is physically attached by, for example, an adhesive bond to a site on the body surface of the patient 20, such as the patient's back.

The surface area of the return electrode 38 in contact with the patient 20 is relatively large in comparison with the surface area of the treatment electrode 24. Consequently, at the tissue adjacent to the return electrode 38, the current density flowing from the patient 20 to the return electrode 38 is relatively low in comparison with the current density flowing from the treatment electrode 24 to the patient 20. Because negligible heating is produced at its attachment site to the patient, a non-therapeutic effect is created in the tissue adjacent to the return electrode 38.

Although the treatment electrode 24 and the return electrode 38 are representatively configured for the delivery of monopolar high frequency energy, the treatment electrode 24 may be configured to deliver bipolar high frequency energy. The modifications to the treatment apparatus 10 required to deliver bipolar high frequency energy are familiar to a person having ordinary skill in the art. For example, the return electrode 38 may be eliminated from the treatment apparatus 10 and a bipolar type of treatment electrode substituted for the monopolar treatment electrode 24.

Figure 2:
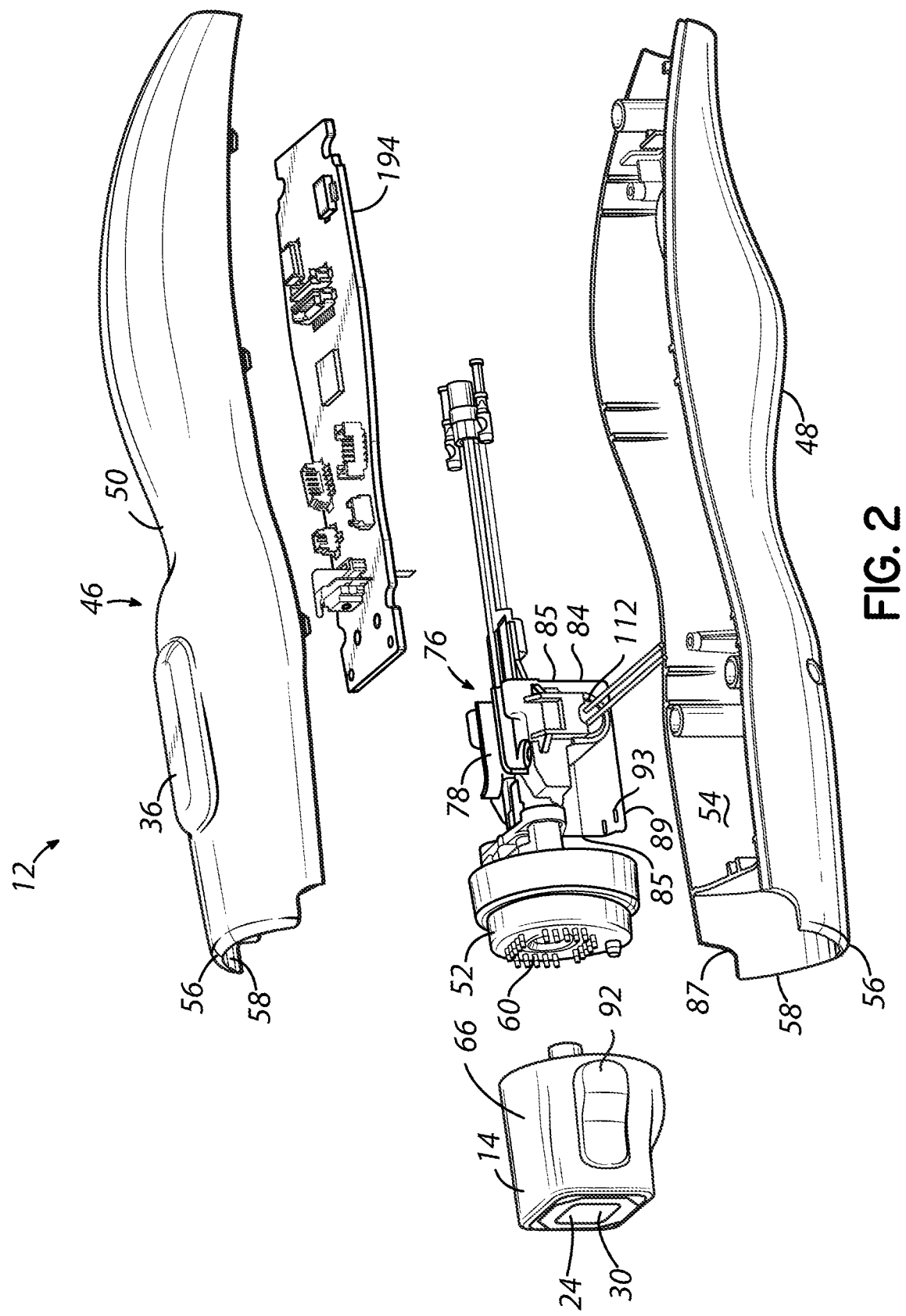
FIG. 2 is an exploded view of a handpiece and a treatment in accordance with an embodiment of the invention.
Figure 3:
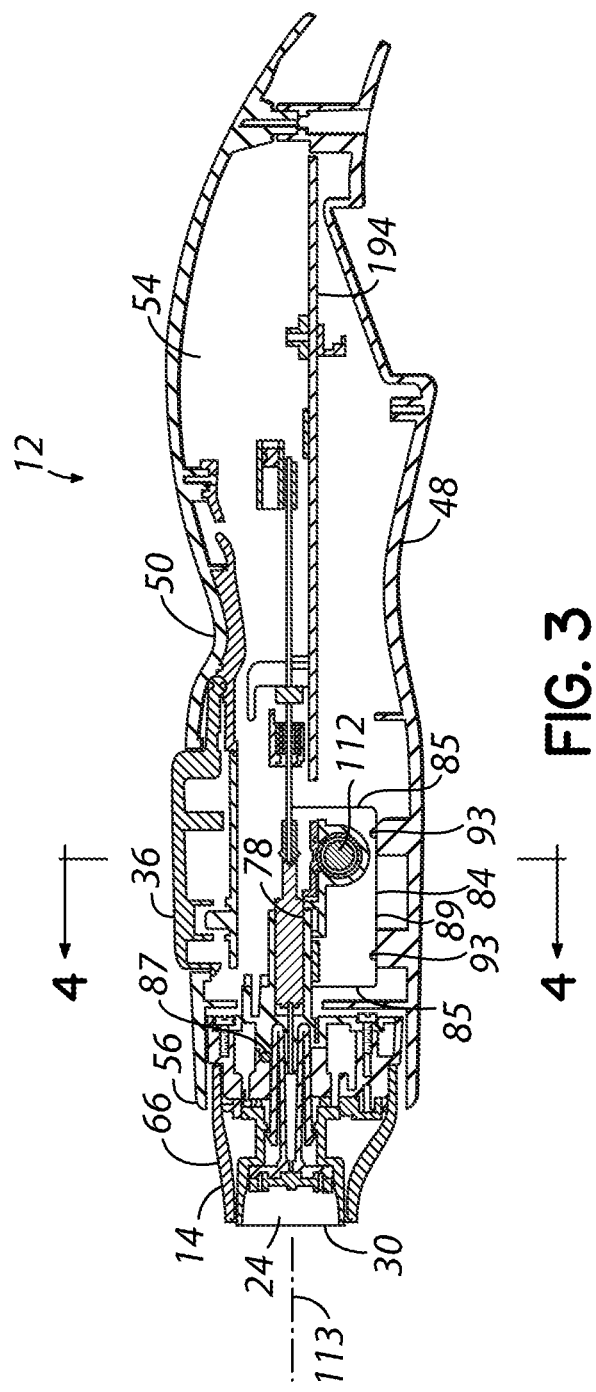
FIG. 3 is a cross-sectional view taken along a major axis of the handpiece and the treatment tip of FIG. 2.
Figure 4:
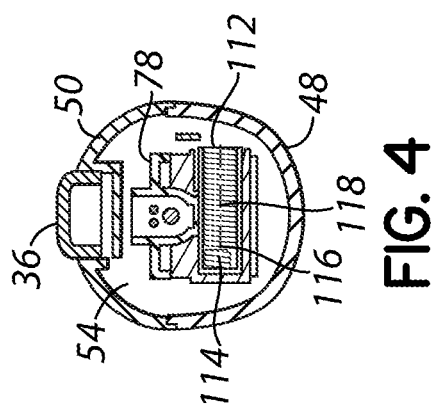
FIG. 4 is front, cross-sectional view of the handpiece and the treatment tip of FIG. 2.

With reference to FIGS. 2-4, the handpiece 12 is constructed from a housing 46 that includes a body 48, a cover 50 assembled by conventional fasteners with the body 48, and an electrical/fluid interface 52 for the treatment tip 14. The housing 46 may be fabricated by an injection molding process using a suitable polymer resin as a construction material. The body 48 and cover 50 constitute shell halves that are integrally fastened together as an assembly. The housing 46 encloses an interior cavity 54 bounded on one side by an interior surface of the body 48 and bounded on the other side by an interior surface of the cover 50. After the body 48 and cover 50 are assembled, the handpiece 12 has a smoothly contoured shape suitable for gripping and manipulation by an operator. The operator maneuvers the treatment tip 14 and treatment electrode 24 to a location proximate to the skin surface 34 and, typically, to place the treatment electrode 24 in proximity with the skin surface 34.

The housing 46 includes a nose 56 and a window 58 in the nose 56 that is sized for the insertion and removal of the treatment tip 14. The electrical/fluid interface 52 is disposed between the window 58 and the interior cavity 54 enclosed inside the housing 46. The treatment tip 14 is sized to be inserted through the window 58 and configured to be physically engaged with the handpiece 12, as described below. In the engaged state, the contact pads carried on the substrate 30 of the treatment electrode 24 establish respective electrical contacts with complementary electrical contacts 60, such as pogo pins, carried by the electrical/fluid interface 52 of the handpiece 12. These electrical contacts 60 are electrically coupled with one or more of the conductors (not shown) that extend from the handpiece 12 to the generator 26 and system controller 18.

The treatment tip 14 is released for removal from the handpiece 12 by gripping the tip 14 using finger grips 92 and removing the tip 14 from the grip ring 87. After separation from the handpiece 12, the treatment tip 14 may be discarded or may be retained for a future treatment procedure.

The handpiece 12 of the treatment apparatus 10 incorporates a vibrator or vibration device, generally indicated by reference numeral 76. The vibration device 76 is configured to oscillate or vibrate the treatment tip 14 and the treatment electrode 24 at a relatively low frequency relative to the handpiece 12 and the skin surface 34. In particular, the vibration device 76 causes the treatment tip 14 to oscillate or vibrate in a linear path along an axis 74 that is normal or substantially normal to the skin surface 34 (shown in FIGS. 5 and 6) with a portion of the treatment electrode 24 in contact with the skin surface 34 to transfer the vibration to the skin surface 34.

The vibration device 76 generally includes a carriage 78, a hinged bracket in the form of a leaf spring 84, and a vibration motor 112. The carriage 78 is located within the interior cavity 54 of the housing 46 and may support the electrical/fluid interface 52 that is coupled with the treatment tip 14. The leaf spring 84 includes spring arms 85 and a spring body 89 located proximate to the interior cavity 54 of the body 48 of the housing 46. The vibration motor 112 is located in a space framed or formed by the spring arms 85 and the spring body 89.

The carriage 78 is attached to the electrical/fluid interface 52, the leaf spring 84, and the vibration motor 112. In this way, when the vibration motor 112 operates as detailed below, the carriage 78 oscillates the electrical/fluid interface 52, which in turn oscillates or vibrates the treatment tip 14 in a bi-directional and reciprocating manner along axis 74 as best shown in FIGS. 5 and 6.

The leaf spring 84 is mounted to the interior cavity 54 by directly mounting the spring body 89 to fastener boss locations 93. As vibration motor 112 operates to cause vibration as detailed below, the leaf spring 84 suppresses vibration of the treatment tip 14 in all directions except in a direction along the axis 74 that is normal or substantially normal to the skin surface 34 (best shown in FIGS. 5 and 6) with a given positive vibration amplitude (FIG. 5) and a given vibration amplitude (FIG. 6).

The vibration motor 112 is installed with an axis of rotation that is transverse to a longitudinal axis 113 of the handpiece 12, as best shown in FIG. 4. An exemplary vibration motor 112 is a rotary vibrator that may be an eccentric rotating mass vibration motor ("ERM motor"). In a typical ERM motor, an off-center or eccentric counterweight 114 is attached to one end of an output shaft 116 of the vibration motor 112. The counterweight 114 is spun by the vibration motor 112 about an axis of rotation 118 that is generally collinear with the output shaft 116. The counterweight 114 has a center of mass 115 that is offset or spaced apart from the axis of rotation 118 of the output shaft 116. As a result, the center of mass of the counterweight 114 and the axis of rotation 118 of the output shaft 116 are not collinear. When the vibration motor 112 is energized and operating to spin the counterweight 114, the off-balance motion of the mass of the counterweight 114 induces a vibration in the vibration motor 112, which is transferred from the vibration motor 112 to the carriage 78 and treatment tip 14 through elastic deflections of the leaf spring 84.

The treatment tip 14 may include, for example, a tip frame as described in U.S. Pat. No. 8,882,758, issued Nov. 11, 2014, entitled "Tissue Treatment Apparatus and Systems with Pain Mitigation and Methods for Mitigating Pain During Tissue Treatments," which is hereby incorporated by reference herein in its entirety. The tip frame may contact the skin surface 34 and space a peripheral portion of the treatment electrode 24 from the skin surface 34. A portion of the rigid outer shell 66 of the treatment tip 14 encircling the treatment electrode 24 may be in a contacting relationship the skin surface 34. In each instance, the vibration may be transferred at least in part by a structural contact other than the portion of the treatment electrode 24 in contact with the skin surface 34.

In an embodiment, the vibration motor 112 may be a direct current (DC) motor that is controlled by a DC drive voltage supplied from a power supply (not shown) at the system controller 18 through at least one of the insulated and shielded conductors (not shown). The DC drive voltage energizes the motor windings and rotates the output shaft 116 and counterweight 114, preferably at a constant angular velocity, about the axis of rotation 118. The treatment tip 14 will cyclically move from the negative vibration amplitude to the positive vibration amplitude (FIG. 5) and then from the positive vibration amplitude to the negative vibration amplitude (FIG. 6) as the counterweight 114 rotates about the axis of rotation 118. The vibration amplitude, A, typically increases in magnitude inversely proportionate to the magnitude of DC drive voltage used to control the motor 112. Increasing the DC drive voltage will increase the vibration frequency, which is proportional to the angular velocity of the counterweight 114 about the axis of rotation 118.

In an alternative embodiment, the DC drive voltage may control the motor 112 to bi-directionally rotate the counterweight 114 and output shaft 116 about the axis of rotation 118. The direction of rotation of the counterweight 114 about the axis of rotation 118 is alternated with an appropriate drive waveform for the DC drive voltage. The counterweight 114 travels through only a portion of a full revolution of the output shaft 116 before the counterweight 114 changes direction and moves in the opposite direction. This causes a vibration in the vibration motor 112 and in the carriage 78 coupled to the vibration motor 112 and leaf spring 84 as the counterweight 114 is rapidly moved back and forth in a cyclic rocking motion relative to the axis of rotation 118.

The vibration amplitude, A, of the treatment tip 14 can also be increased or decreased, respectively, by increasing or decreasing the mass and/or geometrical shape of the counterweight 114. The greatest magnitude for the vibration amplitude, A, may be output near a resonance frequency of the vibration device 76.

In the representative embodiment, the counterweight 114 has a cylindrical shape. However, other types and geometrical shapes of counterweight 114 can be used. For example, the counterweight 114 may be wedge-shaped or pie-shaped eccentric with one end of the eccentric coupled to the output shaft 116 so that the majority of the mass extends to one side of the output shaft 116. The offset between the center of mass 115 of the counterweight 114 and the axis of rotation of the output shaft 116 can be adjusted in different device embodiments to provide stronger or weaker vibrations, as desired to achieve a particular pain management effect.

In various embodiments, the vibration frequency may be on the order of 100 Hz to 1 kHz, preferably between in a range of 100 Hz to 300 Hz. In some embodiments, the vibration frequency may be at least 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, or 300 Hz. In some embodiments, the vibration frequency may be at most 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, or 300 Hz. In some embodiments, the vibration frequency may be about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, or 300 Hz. In some embodiments, the vibration frequency may be about 100 Hz to about 110 Hz, or about 110 Hz to about 120 Hz, or about 120 to about 130 Hz, or about 130 Hz to about 140 Hz, or about 140 Hz to about 150 Hz, or about 150 Hz to about 160 Hz, or about 160 Hz to about 170 Hz, or about 170 Hz to about 180 Hz, or about 180 Hz to about 190 Hz, or about 190 Hz to about 200 Hz, or about 200 Hz to about 210 Hz, or about 210 Hz to about 220 Hz, or about 220 Hz to about 230 Hz, or about 230 Hz to about 240 Hz, or about 240 Hz to about 250 Hz, or about 250 Hz to about 260 Hz, or about 260 Hz to about 270 Hz, or about 270 Hz to about 280 Hz, or about 280 Hz to about 290 Hz, or about 290 Hz to about 300 Hz.

The window 58 of the handpiece 12 is preferably dimensioned in relation to the extent of the vibration amplitude, A, such that the outer shell 66 of the treatment tip 14 does not contact the housing 46 of the handpiece 12 when vibrated. The clearance ensures that the handpiece 12 does not interfere with the vibration of the treatment tip 14.

One or more printed circuit boards 194 may be located inside the interior cavity 54. Each of the printed circuit boards 194 may carry electrical circuitry with electronic components that support the operation and functionality of the treatment apparatus 10.

In use to perform a treatment procedure, the physician selects a type of treatment tip 14 based on the procedure to be performed and the size of the surface area on the patient 20 to be treated, as well as the depth of cooling and heating desired for the treatment procedure. The procedure protocol may include a combination of pulse count, pulse duration, energy level, and heating profile. After choosing the treatment tip 14 and attaching it to the handpiece 12, the physician marks the intended treatment area on the patient 20 with a grid of removable markings that are easily wiped away post-procedure. Each discrete square in the grid corresponds approximately to the size of the portion of the treatment electrode 24 that is placed in direct contact with the skin surface 34. The markings operate as a placement guide on the patient's skin surface 34 for the treatment procedure. The return electrode 38 is attached to the patient 20 to supply the current path 42 for the high frequency current back to the generator 26.

After the application of a conductive fluid onto the skin surface 34, each square within the grid is sequentially treated with high frequency energy delivered from the treatment electrode 24 in a stamping mode of operation. Specifically, at each grid square, the physician lands the portion of treatment electrode 24 directly against the patient's skin and actuates the activation button 36 on the handpiece 12. The handpiece 12 processes information from the treatment tip 14 about skin temperature and contact, treatment force or pressure against the skin, cooling system function, and other types of relevant data. This information is sent from the handpiece 12 to the console 16 in order to generate the proper high frequency signal at the generator 26. Instead of a stamping mode in which the treatment electrode 24 is lifted and repositioned to treat grid squares on the skin surface 34, the handpiece 12 may be continuously moved over the treatment area without lifting the treatment electrode 24 from the skin surface 34.

Under the control of the system controller 18, a control valve (not shown) regulates the delivery of cryogen, which cools and protects the skin's superficial layers proximate to the skin surface 34. The cryogen is used to pre-cool the patient's epidermis, before powering the treatment electrode 24, by extracting heat from the warmer skin. The treatment electrode 24 transmits high frequency energy to the skin while serving as a contact cooling membrane for the cryogen. The system controller 18 monitors a combination of inputs, such as temperatures, power levels and delivery duration, to precisely and safely control the high frequency energy and cooling delivery to each treatment site in the grid. Cooling the epidermis limits the temperature to lessen the likelihood of thermal damage to the epidermis. Depths of tissue 32 that are not significantly cooled by pre-cooling will be heated to therapeutic temperatures resulting in the desired therapeutic effect. The amount or duration of pre-cooling may be used to select the protected depth of untreated tissue 32.

The cryogen may also be used to cool the contacted tissue 32 during, before, and/or after heating by the transferred high frequency electromagnetic energy. Various duty cycles of cooling and heating by high frequency energy transfer are utilized depending on the type of treatment and the desired type of therapeutic effect. The cooling and heating duty cycles may be controlled and coordinated by operation of the system controller 18.

After energy delivery is completed, the handpiece 12 is maneuvered to lift the portion of the treatment electrode 24 from the skin surface 34. The handpiece 12 and treatment tip 14 are moved among subsequent treatment locations in the grid and energy is delivered is a similar manner for treating large regions on the patient 20, such as the patient's face. Multiple passes over the entire grid of the treatment zone, separated in time by a quiescent period of few minutes, may be used to enhance the treatment, as is understood by persons skilled in the art. Multiple treatments, which are separated temporally by a lengthier healing period, may be needed for a successful treatment that supplies the desired cosmetic effect.

The treatment depth may be adjusted by, for example, programming different output parameters (i.e., high frequency currents and voltages, duration over which current is applied, etc.) for the high frequency power supplied from generator 26 to the treatment electrode 24. Cooling can be adjusted by providing a pre-treatment cooling period, a concurrent-treatment cooling period, a post-treatment cooling period, as desired, and also by controlling the temperature of the treatment tip 14 during the cooling to be, for example, either extremely cold, medium cooled, or mildly cooled, as desired. The treatment depth may also be contingent upon other variables, such as the specific type of tissue 32 involved in the treatment.

The vibration device 76 is functional during the treatment procedure for vibrating the treatment tip 14 and, in particular, for transferring vibrations from the portion of the treatment electrode 24 to the skin surface 34 and underlying region of the tissue 32 being heated by the high frequency energy. The vibration may be continuous, may be triggered to occur only when the activation button 36 is actuated, or applied a different manner. For example, the vibration device 76 may be activated for the same time period over which energy delivery occurs or for a different time period that is either shorter or longer. For example, the mechanical vibrations may be initiated after the electromagnetic energy delivery is initiated and persist through the remainder of the energy delivery, as well as continue for a given time after energy delivery ceases. The vibration device 76 may be activated to transfer mechanical vibrations through the skin surface 34 and to the tissue 32 before, during, and/or after the delivery of the electromagnetic energy at each grid location to cause heating in a corresponding region of the tissue 32.

The vibration of the treatment tip 14 using the vibration device 76 may decrease the sensation of pain experienced by the patient 20 from the delivery of electromagnetic energy during a treatment procedure. Specifically, in one aspect, the vibration is believed to operate to average the heat applied across the treatment area within each treatment site because the treatment tip 14 and, more specifically, the portion of treatment electrode 24 contacting the skin surface 34 is in continuous motion to vibrate the skin surface and tissue roughly within the boundaries of the grid area. In contrast, the treatment electrodes of conventional treatment tips are held pressed with a constant force of contact with the skin surface 34 during the delivery of electromagnetic energy. The dynamic motion of the portion of the treatment electrode 24 directly contacting the skin surface 34 compensates for hot spot thermal zones of non-uniform higher temperatures, which are highly likely sources of heat pain.

Vibration of the portion of the treatment electrode 24 may also operate to interfere with the ability of nerves in the treated tissue 32 to send heat-related pain signals to the brain of the patient 20. Although not wishing to be limited by theory, it is believed under the gate control theory of pain that the perception of physical pain is not a direct result of activation of nociceptors (sensory neurons or nerve endings that sends signals that cause the perception of pain in response to a potentially damaging stimulus). Instead, the perception of physical pain is modulated by interaction between neurons that transmit pain and neurons that do not transmit pain. The gate control theory of pain teaches that activation of nerves that do not transmit pain signals, such as nerves sensitive to pressure and vibration delivered by the vibration device 76 can interfere with signals from nociceptors and thereby inhibit a patient's perception of pain, such as pain arising from heating of the tissue.

The train of vibrations delivered by the vibration device 76 induces repetitive back and forth movement of the tissue 32 in the treatment area that may act to increase local blood perfusion. Increasing the local blood perfusion may in turn act to increase the temperature loading capabilities of the skin and assist in removing heat.

References herein to terms such as "vertical," "horizontal," etc. are made by way of example, and not by way of limitation, to establish a frame of reference. It is understood that various other frames of reference may be employed for describing the invention without departing from the spirit and scope of the invention. It is also understood that features of the invention are not necessarily shown to scale in the drawings. Furthermore, to the extent that the terms "composed of," "includes," "having," "has," "with," or variants thereof are used in either the detailed description or the claims, such terms are intended to be inclusive and open-ended in a manner similar to the term "comprising."

It will be understood that when an element is described as being "attached," "connected," or "coupled" to another element, it can be directly connected or coupled to the other element or intervening elements may be present. In contrast, when an element is described as being "directly attached," "directly connected," or "directly coupled" to another element, there are no intervening elements present.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described.

Accordingly, departures may be made from such details without departing from the spirit or scope of applicants' general inventive concept.

What is claimed is:

1. A tissue treatment apparatus for use in treating a region of tissue located beneath a skin surface with electromagnetic energy, the tissue treatment apparatus comprising:
   a delivery device configured to transfer the electromagnetic energy through the skin surface to the region of tissue;
   a handpiece coupled in a removable and releasable manner to the delivery device, the handpiece having a longitudinal axis and an electrical/fluid interface coupled to the delivery device; and
   a vibration device mechanically coupled with the delivery device, the vibration device comprising a vibration motor, a carriage, and a leaf spring each positioned inside the handpiece, the leaf spring including a plurality of spring arms and a spring body, the vibration motor located in a space framed by the spring arms and the spring body, the carriage attached to the electrical/fluid interface, the leaf spring, and the vibration device, the vibration device having an axis of rotation that is aligned transverse to the longitudinal axis of the handpiece, and the vibration device configured to transfer mechanical vibrations through the skin surface to the region of tissue along an axis that is substantially normal to the skin surface.

2. The tissue treatment apparatus of claim 1 wherein the vibration motor includes an eccentric rotating mass.

3. The tissue treatment apparatus of claim 2 wherein the leaf spring is configured to elastically deflect such the delivery device is constrained to vibrate in a direction of the axis.

4. The tissue treatment apparatus of claim 1 wherein the vibration device is configured to transfer the mechanical vibrations at a vibration frequency within a range of 100 Hz to 1 kHz.

5. The tissue treatment apparatus of claim 1 wherein the vibration device is configured to transfer the mechanical vibrations at a vibration frequency within a range of 100 Hz to 300 Hz.

6. The tissue treatment apparatus of claim 1 wherein the carriage is configured to oscillate the delivery device along the axis in a bi-directional and reciprocating manner.

7. The tissue treatment apparatus of claim 1 wherein the carriage is configured to oscillate the delivery device in a linear path along the axis.

8. The tissue treatment apparatus of claim 1 wherein the carriage is configured to oscillate the delivery device in a linear path along the axis in a bi-directional and reciprocating manner.

* * * * *